United States Patent [19]

Hallenbach et al.

[11] Patent Number: 4,847,382

[45] Date of Patent: Jul. 11, 1989

[54] 5-AMINOPYRIDINE COMPOUNDS

[75] Inventors: Werner Hallenbach, Langenfeld; Hans Lindel, Leverkusen, both of Fed. Rep. of Germany

[73] Assignee: Bayer Aktiengesellschaft, Leverkusen, Fed. Rep. of Germany

[21] Appl. No.: 161,539

[22] Filed: Feb. 29, 1988

Related U.S. Application Data

[63] Continuation-in-part of Ser. No. 040,509, Apr. 20, 1987.

[30] Foreign Application Priority Data

Mar. 7, 1987 [DE] Germany ............... 3707361
Mar. 13, 1987 [DE] Germany ............... 3708093

[51] Int. Cl.[4] .................................. C07D 239/02
[52] U.S. Cl. ................................ 546/311; 546/312
[58] Field of Search ............... 546/311, 312; 514/349

[56] References Cited

U.S. PATENT DOCUMENTS 4,358,455 11/1982 Atkinson et al. ............... 546/270

FOREIGN PATENT DOCUMENTS 0154537 3/1982 German Democratic Rep. .................... 546/260

OTHER PUBLICATIONS

Brignell et al., "The Kinetics and Mechanism of Electrophilic Substitution . . .," J. Chem. Soc. (B) (1970), pp. 117-121.
Cooper et al., "Synthesis of 5-Acetamido-2-acetylpiperidine," J. Chem. Soc. (C) 1971, pp. 772-776.

Primary Examiner—Mary C. Lee
Assistant Examiner—Zinna Northington
Attorney, Agent, or Firm—Sprung Horn Kramer & Woods

[57] ABSTRACT

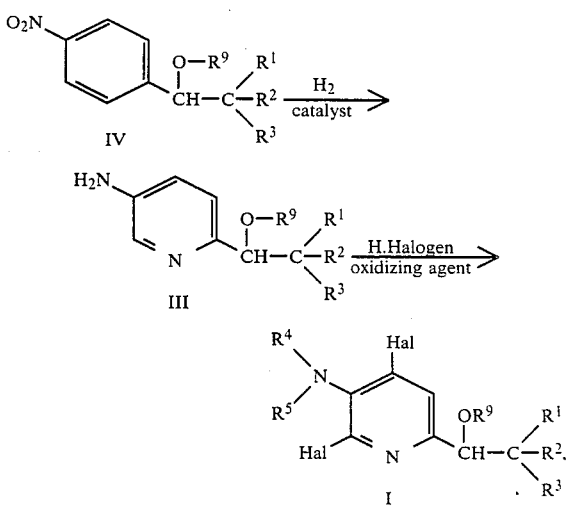

in which
R[1] represents hydrogen, —O—R[7] or —NHR[8],
R[2] represents hydrogen or halogen,
R[3] represents hydrogen or, together with R[2], represents =O,
R[4] represents hydrogen or alkyl,
R[5] represents hydrogen, alkyl, halogenoalkyl or aryl,
R[7] represents alkyl,
R[8] represents alkyl, cyloalkyl, aralkyl, aryl or heterocyclyl, which can optionally be substituted,
R[9] represents acyl or hydrogen and Hal represents halogen.

Compounds III are new. Compounds I are known as yield-promoting agents in animal feeds.

3 Claims, No Drawings

5-AMINOPYRIDINE COMPOUNDS

This is a continuation-in-part of Application Ser. No. 40,509, filed Apr. 20, 1987, now pending.

The present invention relates to a new process for the preparation of 5-amino-4,6-dihalogenopyridines by halogenation of the corresponding 5-aminopyridines with a hydrogen halide acid in the presence of oxidizing agents.

The halogenation of 5-nitropyridines substituted in the 2-position is known. The bromination of 2-amino-5-nitropyridine takes place in the 3-position; R. H. Brignell J. Chem. Soc. (B) (1970) 117-21. If the 3-position is substituted, for example in the case of 3-amino-pyridine, the halogenation with a hydrogen halide acid in the presence of oxidizing agents takes place in the 2-position (O. V. Schickh et al. Ber. dt. Chem. Ges. 69, 2593-2605).

Nothing was known of the selective halogenation of 2-substituted 5-aminopyridines in the 4,6-position.

The following have been found:

1. Process for the preparation of 5-amino-4,6-dihalogenopyridine derivatives of the formula

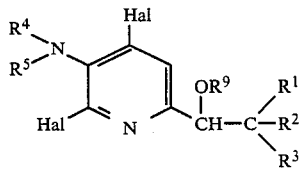

in which
R$^1$ represents hydrogen, —O—R$^7$ or —NHR$^8$,
R$^2$ represents hydrogen or halogen,
R$^3$ represents hydrogen or, together with R$^2$, represents =O,
R$^4$ represents hydrogen or alkyl,
R$^5$ represents hydrogen, alkyl, halogenoalkyl or aryl,
R$^7$ represents alkyl,
R$^8$ represents alkyl, cyloalkyl, aralkyl, aryl or heterocyclyl, which can optionally be substituted,
R$^9$ represents acyl or hydrogen and
Hal represents halogen, characterized in that compounds of the formula II

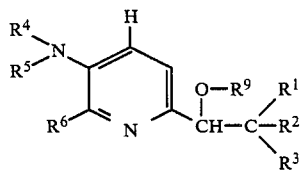

in which
R$^1$-R$^5$ have the abovementioned meaning,
R$^6$ represents hydrogen or halogen and
R$^9$ represents acyl or hydrogen, are halogenated with hydrogen halide acids in the presence of oxidizing agents.

2. 5-Aminopyridines of the formula III

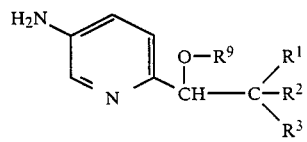

in which
R$^1$ represents hydrogen, —O—R$^7$ or —NHR$^8$,
R$^2$ represents hydrogen or halogen,
R$^3$ represents hydrogen or, together with R$^2$, represents =O,
R$^9$ represents acyl or hydrogen and
R$^7$-R$^8$ have the meanings given above, are new.

3. Process for the preparation of 5-aminopyridines of the formula III

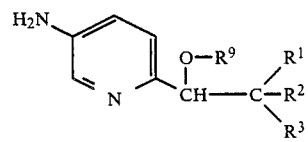

in which
R$^1$, R$^2$, R$^3$ and R$^9$ have the meanings given above, characterized in that 5-nitropyridines of the formula IV

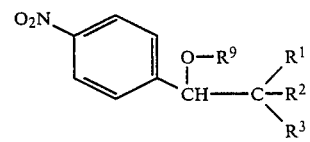

in which
R$^1$, R$^2$, R$^3$ and R$^9$ have the meanings given above, are reduced catalytically with hydrogen.

5-Amino-6-halogenopyridines of the formula I and their preparation are also the subject of application Ser. No. 40,509, filed Apr. 20, 1987, now pending. In that application, they are obtained by reacting pyridinealdehydes with isonitriles to give the corresponding α-acetoxy-α-pyridylacetamides and, if appropriate, subsequently hydrolyzing these.

The monohalogenation of 3-aminopyridine was known. However, it was not known that in the case of 2-substituted 5-aminopyridines, dihalogenation takes place selectively in the 4,6-positions if the reaction is carried out with hydrogen halide acids in the presence of oxidizing agents. Thus, for example, halogenation with chlorine or bromine gave perhalogenated products. Mixtures of halogenation products with a varying halogen content would also have been expected in the case of halogenation with a hydrogen halide acid in the presence of oxidizing agents 5-Amino-4,6-dihalogenopyridine derivatives of the formula I which are preferably prepared by the process according to the invention are those in which
R$^1$ represents hydrogen, —O—R$^7$ or —NHR$^8$,
R$^2$ represents hydrogen, chlorine or bromine,
R$^3$ represents hydrogen or, together with R$^2$, represents double-bonded oxygen (carbonyl oxygen),
R$^4$ represents hydrogen or C$_{1-4}$-alkyl,
R$^5$ represents hydrogen, C$_{1-4}$-alkyl, C$_{1-4}$-alkylcarbonyl, benzoyl, benzylsulphonyl, phenylsulphonyl, which is optionally substituted, or $C_{1-4}$-alkylsulphonyl. Possible substituents are CN, halogen, OH, $C_{1-4}$alkyl, $C_{1-4}$-halogenoalkyl, $C_{1-4}$-alkoxy, $C_{1-4}$-halogenoalkoxy, $C_{1-4}$-alkylthio, and $C_{1-4}$-halogenoalkylthio, $R^7$ represents $C_{1-6}$-alkyl, $R^8$ represents optionally substituted $C_{1-6}$-alkyl, $C_{3-6}$-cycloalkyl, $C_{1-6}$-alkylphenyl or phenyl and $R^9$ represents alkylcarbonyl or hydrogen.

Preferred possible substituents of the optionally substituted radicals are: cyano, halogen, such as fluorine or chlorine, hydroxyl, $C_{1-4}$-alkyl, $C_{1-4}$-halogenoalkyl, phenyl, $C_{1-4}$-alkoxy, $C_{1-4}$-halogenoalkoxy, $C_{1-4}$-alkylthio, and $C_{1-4}$-halogenoalkylthio, and in the case where the substituents are on a phenyl radical, also preferably methylenedioxy, ethylenedioxy, halogen-substituted .methylenedioxy and halogen-substituted ethylenedioxy, and furthermore phenyl and phenoxy, which can in turn carry one or more of the abovementioned substituents.

Hal represents chlorine or bromine.

5-Amino-4,6-dihalogenopyridine derivatives of the formula I which are especially preferably prepared by the process according to the invention are those in which $R^1$ represents hydrogen or $-NHR^8$, $R^2$ represents hydrogen or chlorine, $R^3$ represents hydrogen or, together with $R^2$, represents double-bonded oxygen (carbonyl oxygen), $R^4$ represents hydrogen, $R^5$ represents hydrogen, $R^8$ represents hydrogen, $C_{1-6}$-alkyl which is optionally substituted by 1-5 halogen atoms or $C_{3-6}$-cycloalkyl, in particular methyl, ethyl, propyl, butyl and pentyl, secondary and tertiary alkyl radicals being mentioned in particular, $C_{1-6}$-alkylphenyl which can optionally be substituted by halogen, in particular fluorine or chlorine, $C_{1-6}$-alkyl, OH, $C_{1-4}$-alkoxy or optionally halogen-substituted methylenedioxy or ethylenedioxy, or phenyl which can optionally be substituted by halogen, in particular chlorine or fluorine, $C_{1-4}$-alkyl, OH, $C_{1-4}$-alkoxy or optionally halogen-substituted methylenedioxy or ethylenedioxy, $R^9$ represents acetyl or hydrogen and Hal represents chlorine.

The following compounds of the formula I may be mentioned specifically: $R^1=NHR^8$; $R^2+R^3=O$; $R^4$, $R^5=H$; $Hal=Cl$,

| $R^8$ | $R^9$ |
|---|---|
| tert.-Butyl | H |
| tert.-Butyl | $\overset{O}{\underset{\|}{C}}-CH_3$ |
| i-Propyl | H |
| i-Propyl | $\overset{O}{\underset{\|}{C}}-CH_3$ |
| Cyclohexyl | H |
| Cyclohexyl | $\overset{O}{\underset{\|}{C}}-CH_3$ |
| 2-(1-Phenyl)-propyl | H |
| 2-(1-Phenyl)-propyl | $\overset{O}{\underset{\|}{C}}-CH_3$ |
| Methyl | H |
| Methyl | $\overset{O}{\underset{\|}{C}}-CH_3$ |
| i-Butyl | H |
| i-Butyl | $\overset{O}{\underset{\|}{C}}-CH_3$ |
| sec.-Butyl | H |
| sec.-Butyl | $\overset{O}{\underset{\|}{C}}-CH_3$ |

$R^1 = OR^7$; $R^2 = R^3 = O$; $R^4$, $R^5 = H$;

| $R^7$ | $R^9$ |
|---|---|
| $-CH_3$ | H |
| $-CH_3$ | $\overset{O}{\underset{\|}{C}}-CH_3$ |
| $-$Ethyl | H |
| $-$Ethyl | $\overset{O}{\underset{\|}{C}}-CH_3$ |
| $-$i-Propyl | H |
| $-$i-Propyl | $\overset{O}{\underset{\|}{C}}-CH_3$ |

$R^1 = NHR^8$; $R^2$, $R^3 = H$; $R^4$, $R^5 = H$; $R^9 = H$

| $R^8$ |
|---|
| tert.-Butyl |
| i-Propyl |
| Cyclohexyl |
| 2-(1-Phenyl)-propyl |
| Methyl |
| i-Butyl |
| sec.-Butyl |

If 2-(5-aminopyrid-2-yl)-2-acetoxyacetic acid cyclohexylamide is used as the compound of the formula II and HBr is used as the hydrogen halide acid for carrying out the process according to the invention, the course of the reaction can be represented by the following equation:

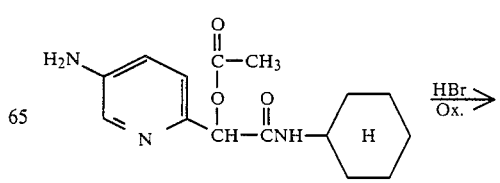

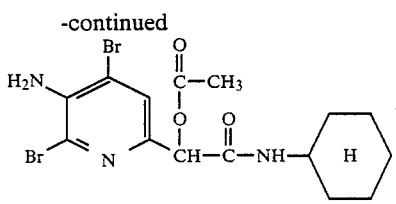

Compounds of the formula II in which the substituents $R^1$–$R^9$ and Hal have the meanings given as preferred and particularly preferred in the case of the compounds of the formula I and $R^9$ represents $C_{1-4}$-alkylcarbonyl, in particular acetyl, are preferably used.

The hydrogen halide acids HCl and HBr are preferably used for the halogenation, and HCl is particularly preferred.

Preferred oxidizing agents which may be mentioned are hydrogen peroxide and salts and derivatives thereof, such as, for example, sodium peroxide, and peracids, such as, for example, aliphatic and aromatic peracids. Peracids which may be mentioned are perpropionic acid and perbenzoic acid, which can optionally be substituted.

Also, salts or esters of hypochlorous acid, such as, for example, sodium hypochlorite, and potassium permanganate, manganese dioxide and peroxomono- and peroxodisulphates.

The hydrogen halide acid is preferably used as an aqueous concentrated acid, particularly preferably as a 20% strength acid.

In the case where monosubstitution is to take place selectively in the 6-position of the pyridine ring, the oxidizing agent is employed in an amount of about one equivalent.

In the case where disubstitution is to take place selectively in the 4- and 6-positions of the pyridine ring, the oxidizing agent is used in an amount of at least 2 equivalents.

The process is preferably carried out in aqueous solution. It can also be carried out in organic solvents which are inert towards the reaction conditions.

The process is carried out at temperatures between 0 and 150° C., preferably between 10 and 100° C. and particularly preferably at 20°–80° C.

The process is carried out under normal pressure.

As already mentioned, the 5-aminopyridines of the formula III are new.

Preferred 5-aminopyridines of the formula III which may be mentioned are those in which the substituents $R^1$, $R^2$ and $R^3$ have the meanings given as preferred and particularly preferred in the case of the compounds and $R^9$ represents $C_{1-4}$-alkylcarbonyl, in particular acetyl.

The following 5-aminopyridines of the formula III may be mentioned specifically:

| | $R^9$ = COCH$_3$; | |
|---|---|---|
| $R^2$ | $R^3$ | $R^1$ |
| | = O | OCH$_3$ |
| | = O | NHC$_4$H$_9$—t |
| | = O | NH—i-Propyl |
| | = O | NH—Cyclohexyl |
| | = O | NH—2-(1-Phenyl)-propyl |
| | = O | NH—Methyl |
| | = O | NH—i-Butyl |
| | = O | NH—s-Butyl |
| H | H | NHC$_4$H$_9$—t |
| H | H | NH—i-Propyl |
| H | H | NH—i-Butyl |

| | $R^9$ = COCH$_3$; | |
|---|---|---|
| $R^2$ | $R^3$ | $R^1$ |
| H | H | NH—s-Butyl |
| H | H | NH—Cyclohexyl |
| H | H | NH—2-(1-Phenyl)-propyl |

If 2-acetoxy-2-(5-nitropyridin-2-yl)acetamide is employed as the starting compound of the formula IV for the preparation of the 5-aminopyridines of the formula II, the process can be represented by the following equation:

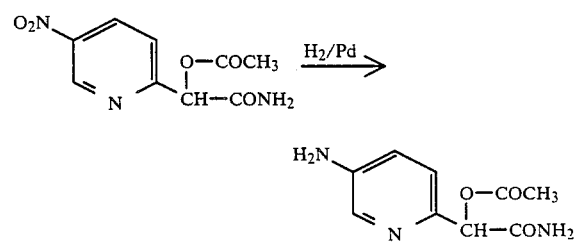

Compounds of the formula IV in which $R^1$, $R^2$, $R^3$ and $R^9$ have the meanings given as preferred and particularly preferred in the case of the compounds of the formula III are preferably used.

The reduction is carried out catalytically with hydrogen in water or organic solvents or solvent mixtures Examples of catalysts which may be mentioned are Raney nickel and palladium-on-active charcoal.

Examples of solvents which may be mentioned are water, ethers, such as, for example, dioxane, aliphatic acids, such as, for example, acetic acid, and solvent mixtures, such as, for example, dioxane/water.

The reduction is carried out at temperatures of 0°–100° C., preferably at room temperature.

The reduction is carried out under a slight increased pressure of hydrogen of about 0.1–1 bar.

Compounds of the formula IV are known per se. They can be obtained, for example, in accordance with the following equation.

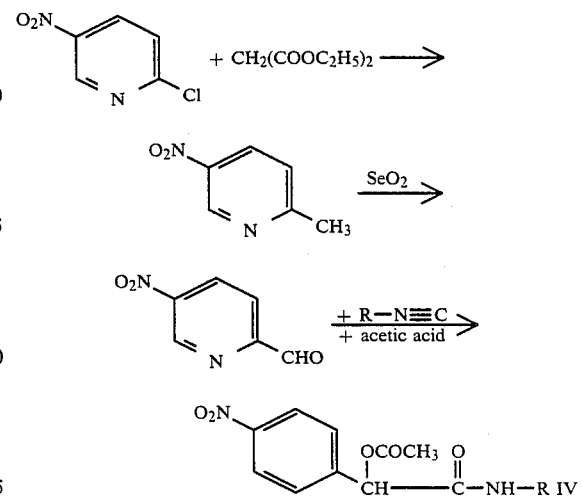

The reaction of 2-chloro-5-nitropyridine with malonic acid esters is known (G. H. Cooper et al. J. Chem.

Soc. (C) 1971, pages 772–776). However, that reaction is carried out in an anhydrous medium in the presence of sodium amide. The reaction can be carried out considerably more easily and less expensively, however, in the presence of alkali metal hydroxides, for example NaOH or KOH, in inert polar aprotic solvents. Solvents which may be mentioned are ethers, such as diethyl ether, dibutyl ether, glycol dimethyl ether, diglycol dimethyl ether tetrahydrofuran or dioxane, nitriles, such as acetonitrile, propionitrile, benzonitrile or glutaric acid dinitrile, dimethylacetamide, N-methylpyrrolidone, dimethyl sulphoxide, tetramethyl sulphone, hexamethylphosphoric acid triamide or t-butanol.

The reaction can also be carried out in the presence of compounds which serve as phase transfer catalysts in two-phase solvent systems.

Such catalysts which may be mentioned are: tetraalkyl- and trialkylaralkyl-ammonium salts with preferably 1 to 10, in particular 1 to 8, carbon atoms per alkyl group, preferably with phenyl as the aryl constituent of the aralkyl group and preferably with phenyl as the aryl constituent of the aralkyl group, and preferably 1 to 4, in particular 1 or 2, carboms atoms in the alkyl part of the aralkyl groups. Possible catalysts here are, above all, the halides, such as the chlorides, bromides and iodides, preferably the chlorides and bromides. Examples which may be mentioned are tetrabutylammonium bromide, benzyl-triethylammonium chloride and methyltrioctylammonium chloride.

In addition to the abovementioned diluents, the following diluents can then be used: aliphatic aromatic, optionally halogenated hydrocarbons, such as pentane, hexane, heptane, cyclohexane, petroleum ether, benzine, ligroin, benzene, toluene, methylene chloride ethylene chloride, chloroform and chlorobenzenes.

The reaction is carried out at −20° to 150° C., preferably at 10° to 50° C. When the reaction has ended, the mixture is neutralized with an acid and the solvent is distilled off or the mixture is poured onto water. However, the mixture can also be boiled with aqueous acid, such as, for example, HCl, without isolation, and the 5-nitropicoline formed can then be extracted, for example with methylene chloride.

Some of the compounds of the formula I have yield-promoting properties in animals. They effect, for example, a shift in the meat-fat ratio in favor of meat in the rearing of animals. Other compounds of the formula I can be converted into such yield-promoting active compounds with the aid of simple processes. In this case, reference is made to application Ser. No. 40,509, supra.

1. PROCESS FOR THE PREPARATION OF 5-AMINO-4,6-DIHALOGENOPYRIDINES

EXAMPLE 1

2-(3-Amino-2-chloro-6-pyridyl)-2-hydroxyacetic acid tert.-butylamide 12 g (45.3 mmol) of 2-(5-amino-2-pyridyl)-2-acetyloxyacetic acid tert.-butylamide are dissolved in 90 ml of concentrated HCl, the solution is preheated to 45° C. and 5.13 ml (45.3 mmol) of 30% strength $H_2O_2$ solution are added dropwise at this temperature in the course of 20 minutes.

The mixture is subsequently stirred for a further 10 minutes, poured onto 750 ml of water and neutralized with 45% strength NaOH. The oil which separates out is taken up in $CHCl_3$ and the aqueous phase is after-extracted again with $CHCl_3$. The combined extracts are washed with $NaHCO_3$ solution, dried with $Na_2SO_4$ and evaporated in vacuo. The residue is chromatographed on silica gel with $CHCl_3$/ethyl acetate.

Yield: 5.8 g (50% of theory), melting point: 136° C.

EXAMPLE 2

2-(3-Amino-2,4-dichloro-6-pyridyl)-2-hydroxyacetic acid tert.-butylamide 10 g (37.7 mmol) of 2-acetoxy-(5-amino-2-pyridyl)-N-tert.-butyl-acetamide are introduced into 75 ml of concentrated HCl, and 10 ml (88.2 mmol) of 30% strength $H_2O_2$ are added dropwise. The exothermic reaction is kept at 50°–55° C. by cooling with ice-water.

When the dropwise addition has ended, the mixture is subsequently stirred for a further 10 minutes and then poured onto 375 ml of water and extracted three times with 200 ml of $CHCL_3$ each time. The extract is washed with $NaHCO_3$ solution, dried and evaporated. The residue is recrystallized from $CHCl_3$/petroleum ether.

Yield: 3.2 g (29%)

Melting point: 177° C.

EXAMPLE 3

N-tert.-Butyl-1-(3-amino-2,4-dichloro-6-pyridyl)-ethanolamine 500 mg (2.4 mmol) of N-tert.-butyl-1-(5-amino-2-pyridyl)-ethanolamine are dissolved in 5 ml of concentrated HCl, and 0.6 ml (5.3 mmol) of 30% strength $H_2O_2$ is slowly added dropwise in the course of 10 minutes. The temperature is thereby kept at 30° C. by cooling. The mixture is subsequently stirred for a further 15 minutes and then poured onto 50 ml of water and rendered alkaline with 6 ml of 45% strength NaOH.

The mixture is extracted three times with $CHCl_3$ and the extracts are dried with $Na_2SO_4$ and evaporated. Residue: 310 mg of a pale brown oil. Content according to HPLC: 55%

2. PROCESS FOR THE PREPARATION OF 5-AMINOPYRIDINES

EXAMPLE 4

2-(5-Amino-2-pyridyl)-2-acetyloxy-acetic acid tert.-butylamide 5 g (16.9 mmol) of 2-acetoxy-2-(5-nitro-2-pyridyl)-N-tert.-butyl-acetamide are dissolved in 50 ml of 90% strength aqueous dioxane, 250 mg of 10% strength palladium-on-active charcoal are added and hydrogenation is carried out at room temperature until the uptake of hydrogen is complete. For working up, the catalyst is filtered off and the filtrate is evaporated. The residue is dried.

Yield: 4.4 g (98%)

Melting point: 180° C.

The following compound was obtained analogously:

EXAMPLE 5

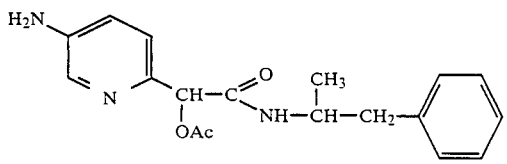

Melting point: 161° C. (diastereomer mixture)

3. PROCESS FOR THE PREPARATION OF 5-NITRO-2-MALONYLPYRIDINES

EXAMPLE 6

Diethyl 5-nitro-2pyridyl-malonate 2.7 g (67.5 mmol) of powdered NaOH are introduced into 10.8 g (675 mmol) of diethyl malonate in 30 ml of dimethylformamide at room temperature, with cooling, a solution of 5 g (31 mmol) of 2-chloro-5-nitropyridine in dimethylformamide is then added dropwise and the mixture is stirred at room temperature until the reaction is complete. For working up, the mixture is poured onto 500 ml of water and acidified with concentrated HCl and the precipitate is filtered off with suction and rinsed with petroleum ether.

Yield: 192 g (content 90%)=97% of theory.

The following yields are obtained analogously in other solvents:

| Solvent | Yield (%) |
| --- | --- |
| Dimethyl sulphoxide | 95 |
| N—Methylpyrrolidone | 97 |
| Tetrahydrofuran | 93 |
| Dioxane | 74 |

EXAMPLE 7

6 g (0.15 mol) of freshly powdered NaOH are introduced into a solution of 25.6 ml (0.15 mol) of diethyl methylmalonate in 100 ml of dimethylformamide, with cooling, and 15.8 g (0.1 mol) of 2-chloro-5-nitropyridine, dissolved in 50 ml of dimethylformamide, are then added dropwise at room temperature, with cooling. The mixture is subsequently stirred for 5 hours and then neutralized with dilute hydrochloric acid and poured onto 1 l of water. The oil which separates out is taken up in 300 ml of methylene chloride and the mixture is washed twice more with water, dried with $Na_2SO_4$ and evaporated in vacuo.

Residue: 30.2 g; content: 88% (HPLC)

Yield: 89.8% of theory.

EXAMPLE 8

2.6 ml (15 mmol) of diethyl methylmalonate are dissolved in 50 ml of methylene chloride, 1.59 g (10 mmol) of 2-chloro-5-nitropyridine and 0.6 g (15 mmol) of tetrabutylammonium chloride are added and the mixture is stirred at room temperature for 4 hours. For working up, 100 ml of water are added and the mixture is neutralized with hydrochloric acid. The organic phase is separated off and washed twice more with water. After the solvent has been evaporated off, 3.12 g remain, with a content of 86% of product (92.3% of theory).

4. PROCESS FOR THE PREPARATION OF 5-NITRO-2-ALKYLPYRIDINES

EXAMPLE 9

5-Nitro-2-picoline 206 g (1.29 mol) of diethyl malonate are added to 600 ml of dimethylformamide, and 51.2 g (1.28 mol) of freshly powdered NaOH are introduced, with cooling. The mixture is subsequently stirred after 15 minutes and a solution of 94.8 g (0.6 mol) of 5-nitro-2-chloropyridine in 600 ml of dimethylformamide is then added dropwise at room temperature. The deep red solution formed is stirred until the reaction is complete, 36% strength HCl is then added dropwise until the color changes to orange and the mixture is evaporated to dryness in vacuo. The residue is taken up in 400 ml of $CHCl_3$, washed with 500 ml of water and evaporated again. The residue is now dissolved in a mixture of 1,200 ml of 36% strength HCl and 870 ml of water and the solution is boiled under reflux until the evolution of gas has ended. Thereafter, it is evaporated in vacuo, the residue is dissolved in 500 ml of water, the solution is extracted with methylene chloride and the organic phase is washed again with water. After the solvent has been stripped off, 72 g (87%) of 5-nitro-2-picoline remain.

Melting point: 109°–111° C.

It will be understood that the specification and examples are illustrative but not limitative of the present invention and that other embodiments within the spirit and scope of the invention will suggest themselves to those skilled in the art.

What is claimed is:

1. A 5-aminopyridine of the formula

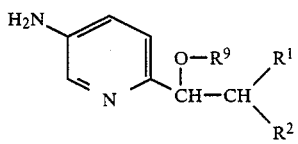

III in which $R^1$ is hydrogen or $-O-C_{1-6}$-alkyl, $R^2$ is hydrogen or halogen, and $R^9$ is alkylcarbonyl or hydrogen.

2. A 5-amino-pyridine of the formula

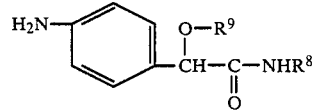

in which $R^8$ is hydrogen, $C_{1-6}$-alkyl which is optionally substituted by 1–5 halogen atoms or $C_{3-6}$-cycloalkyl, $C_{1-6}$-alkylphenyl which is optionally substituted by halogen, $C_{1-6}$-alkyl, OH, $C_{1-4}$-alkoxy or optionally halogen-substituted methylenedioxy or ethylenedioxy, or phenyl which is optionally substituted by halogen, $C_{1-4}$-alkyl, OH, $C_{1-4}$-alkoxy or optionally halogen-substituted methylenedioxy or ethylenedioxy, and $R^9$ is alkylcarbonyl or hydrogen.

3. A 5-amino-pyridine according to claim 2, in which $R^9$ is acetyl.

* * * * *

UNITED STATES PATENT AND TRADEMARK OFFICE
CERTIFICATE OF CORRECTION

PATENT NO. : 4,847,382
DATED : July 11, 1989
INVENTOR(S) : Werner Hallenbach, et al It is certified that error appears in the above-identified patent and that said Letters Patent is hereby corrected as shown below:

| | |
|---|---|
| Col. 3, line 3 | Beginning of line, after "$C_{1-4}$" insert -- - -- |
| Col. 6, line 31 | After "mixtures" insert --.-- |
| Col. 8, line 17 | Delete "$CHCL_3$" and substitute --$CHCl_3$-- |
| Col. 9, line 8 | After "nitro-2" insert -- - -- |
| Col. 9, line 21 | Before "97 %" delete "=" and substitute -- = -- |
| Col. 10, line 50 | Delete formula and substitute 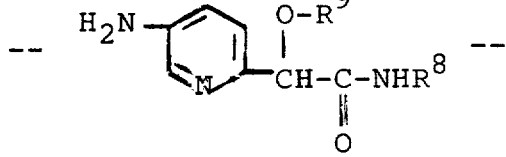 |

Signed and Sealed this

Fifteenth Day of January, 1991

Attest:

HARRY F. MANBECK, JR.

Attesting Officer

Commissioner of Patents and Trademarks